(12) United States Patent
Desi Reddy et al.

(10) Patent No.: US 9,643,939 B1
(45) Date of Patent: May 9, 2017

(54) PROCESS FOR THE PREPARATION OF LINEZOLID

(71) Applicant: Optimus Drugs Private Limited, Hyderabad (IN)

(72) Inventors: Srinivas Reddy Desi Reddy, Hyderabad (IN); Subba Reddy Peketi, Hyderabad (IN); Dnyandev Ragho Rane, Hyderabad (IN); Venkata Srinivasa Rao Velivela, Hyderabad (IN)

(73) Assignee: Optimus Drugs Private Limited, Hyderabad, IN (US)

( * ) Notice: Subject to any disclaimer, the term of this patent is extended or adjusted under 35 U.S.C. 154(b) by 0 days.

(21) Appl. No.: 15/222,003

(22) Filed: Jul. 28, 2016

(30) Foreign Application Priority Data

Apr. 18, 2016 (IN) .......................... 201641013830A

(51) Int. Cl.
*C07D 263/24* (2006.01)

(52) U.S. Cl.
CPC ........ *C07D 263/24* (2013.01); *C07B 2200/07* (2013.01)

(58) Field of Classification Search
CPC .................................................. C07D 263/24
See application file for complete search history.

(56) References Cited

U.S. PATENT DOCUMENTS

| 5,608,110 A | 3/1997 | Ramalingam et al. |
| 5,688,792 A | 11/1997 | Barbachyn et al. |
| 6,875,875 B2 | 4/2005 | Furukawa et al. |

FOREIGN PATENT DOCUMENTS

| WO | WO 99/24393 A1 | 5/1999 |
| WO | WO 2005/099353 A2 | 10/2005 |
| WO | WO 2006/008754 A1 | 1/2006 |
| WO | WO 2007/116284 A1 | 10/2007 |

*Primary Examiner* — Rebecca Anderson
(74) *Attorney, Agent, or Firm* — Ladas+Parry LLP

(57) ABSTRACT

The present invention relates to an improved process for the preparation of Linezolid. More specifically, the present invention relates to an improved process for preparing (S)—N-[[3-[3-fluoro-4-[4-morpholinyl]phenyl]-2-oxo-5-oxazolidinyl]methyl] phthalimide and (S)-glycidyl phthalimide intermediates, which are used in the preparation of Linezolid.

3 Claims, No Drawings

PROCESS FOR THE PREPARATION OF LINEZOLID

FIELD OF THE INVENTION

The present invention relates to an improved process for the preparation of Linezolid. More specifically, the present invention relates to an improved process for preparing(S)—N-[[3-[3-fluoro-4-[4-morpholinyl]phenyl]-2-oxo-5-oxazolidinyl]methyl]phthalimide and (S)-glycidylphthalimide intermediates, which are used in the preparation of Linezolid.

BACKGROUND OF THE INVENTION

Linezolid is a synthetic antibiotic, the first of the oxazolidinone class, used for the treatment of infections caused by multi-resistant bacteria including *streptococcus* and methicillin-resistant *Staphylococcus aureus* (MRSA). The antibacterial effect of oxazolidinones is by working as protein synthesis inhibitors targeting an early step involving the binding of N-formylmethionyl-t-RNA to the ribosome.

Linezolid is marketed by Pfizer under the trade name "Zyvox" and it is chemically known as (S)—N-[[3-(3-fluoro-4-morpholinylphenyl)-2-oxo-5-oxazolidinyl]methyl] acetamide having the formula (I).

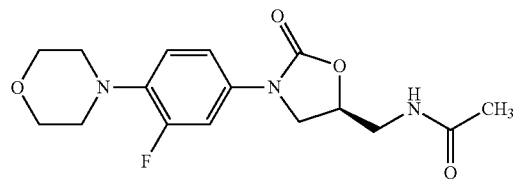

Linezolid is first disclosed in U.S. Pat. No. 5,688,792 and its process comprises the use of R-glycidylbutyrate which results in the formation of (R)—N-[[3-[3-fluoro-4-morpholinyl] phenyl]-2-oxo-5-oxazolidinyl] methanol which in the subsequent stages has to be converted to various intermediary compounds to finally form Linezolid. Said process, which is depicted in the scheme-I given below, also encompasses an intermediary azide compound, which is difficult to handle at industrial level:

Scheme-I

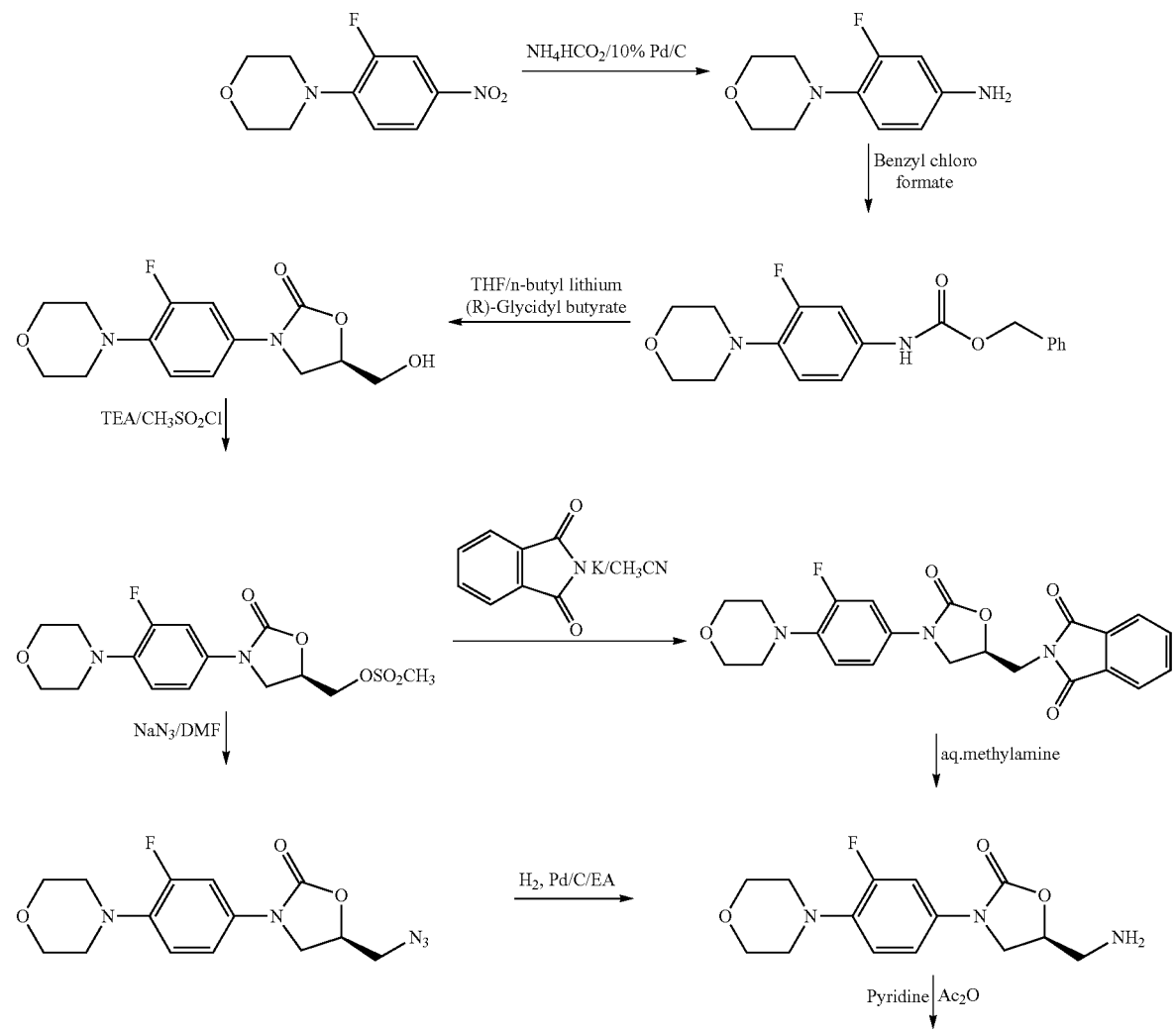

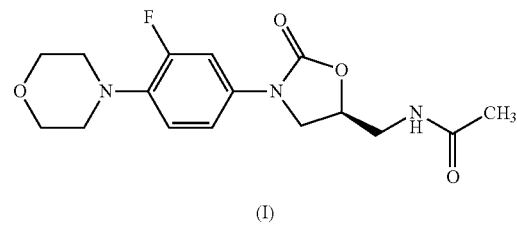

(I)

WO 1999/24393 A1 discloses a process for the preparation of oxazolidinone derivatives, which is depicted in scheme-II given below:

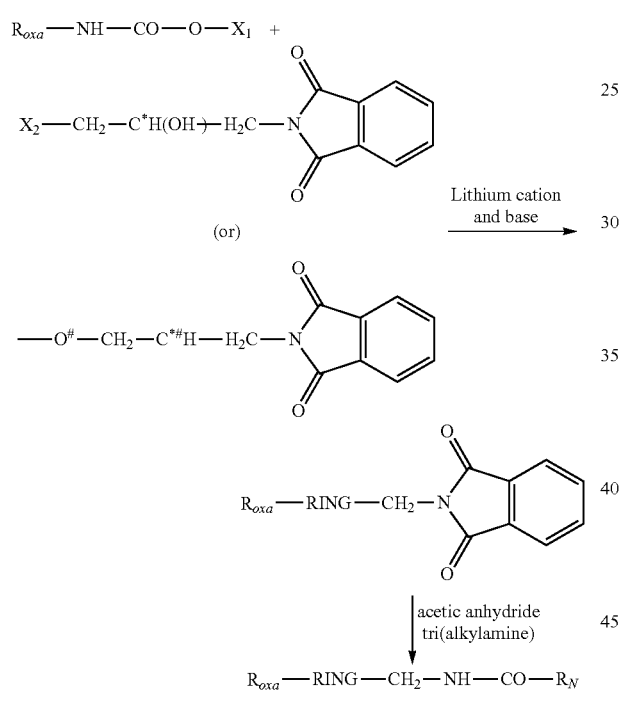

where $R_{oxa}$ is phenyl substituted with one fluoro and one substituted amino group, wherein the substituted amino groups include 4-(benzyloxycarbonyl)-1-piperazinyl, 4-morpholinyl and 4-hydroxyacetylpiperazinyl $X_1$ is $C_1$-$C_{20}$ alkyl;
$X_2$ is Cl, Br
$R_N$ is $C_1$-$C_5$ alkyl
# indicates that the atoms marked with a (#) are bonded to each other resulting in the formation of ring
and RING is

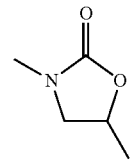

However, WO' 393 does not disclose any specific examples or suitable conditions for the preparation of Linezolid.

WO 2005/099353 A2 discloses a process for the preparation of Linezolid, which is depicted in scheme-III given below:

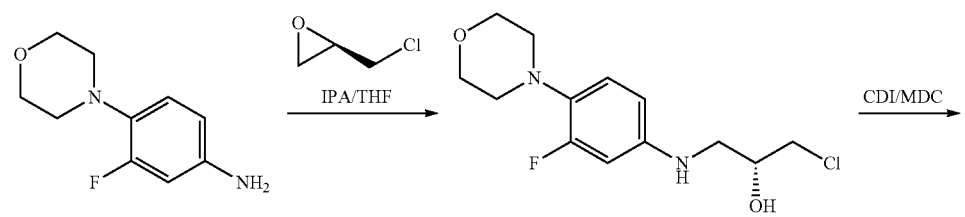

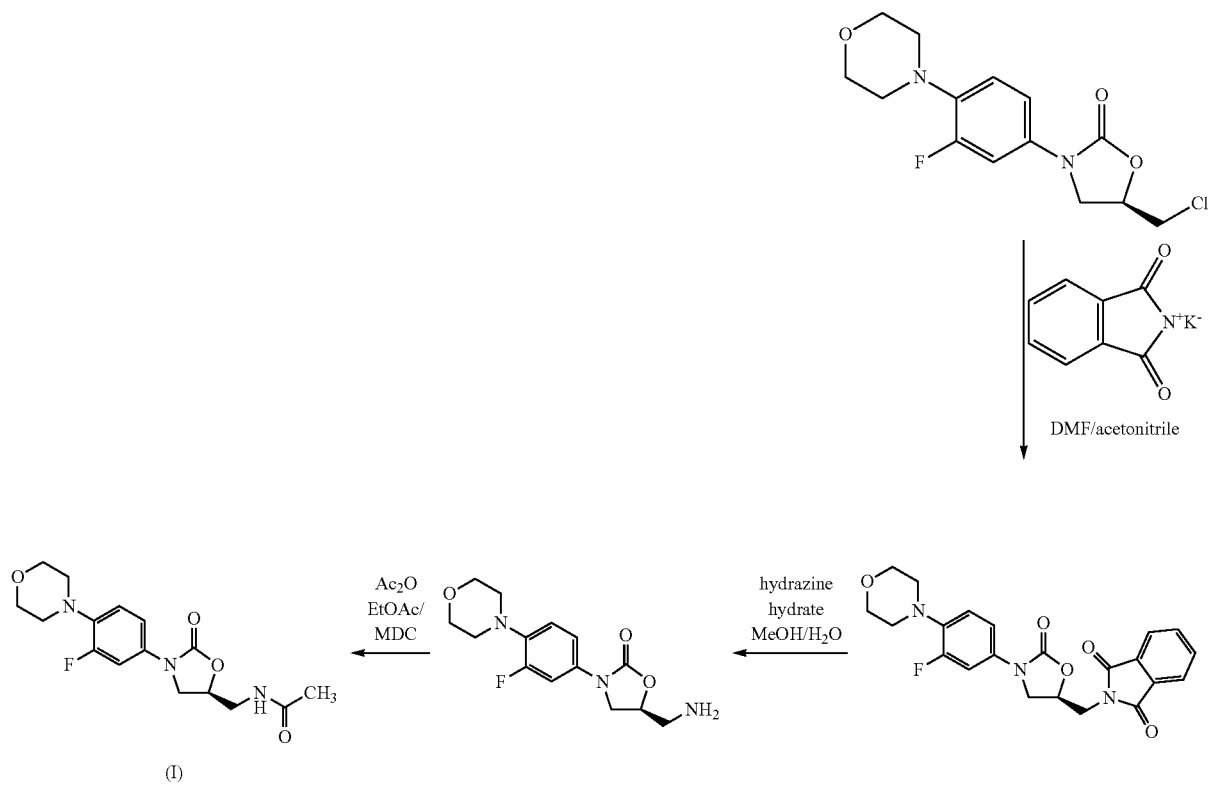
WO 2006/008754 A1 discloses a process for the preparation of Linezolid, which is depicted in scheme-IV given below
Scheme-IV
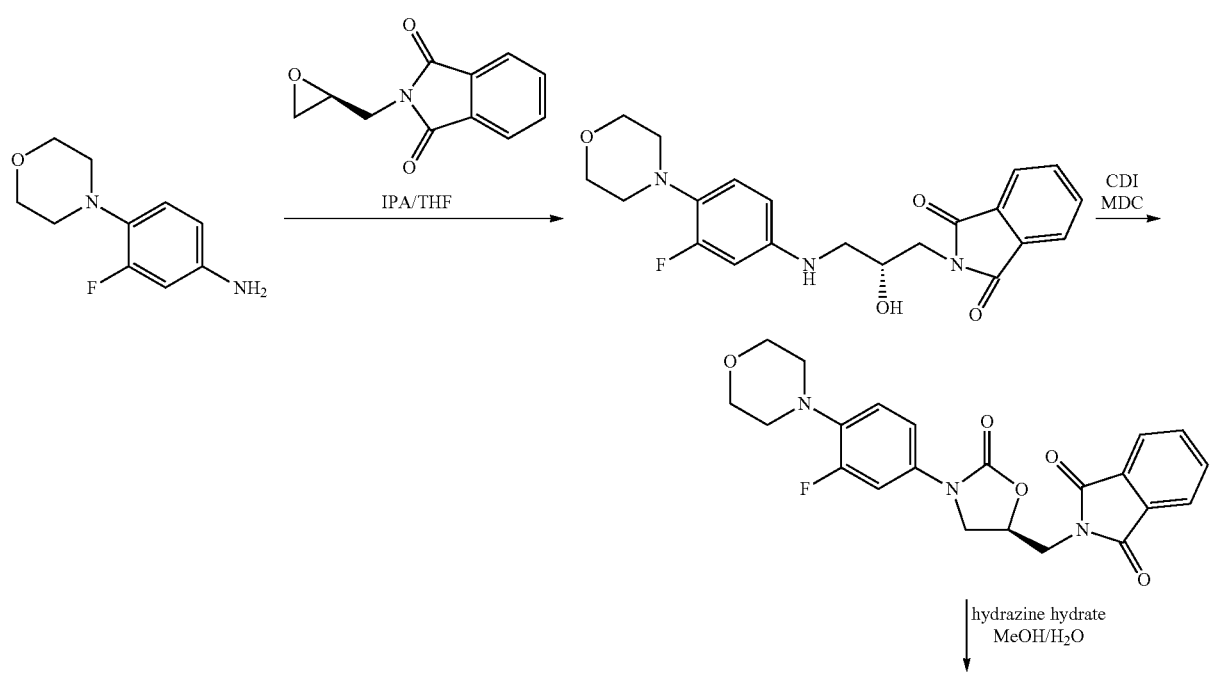

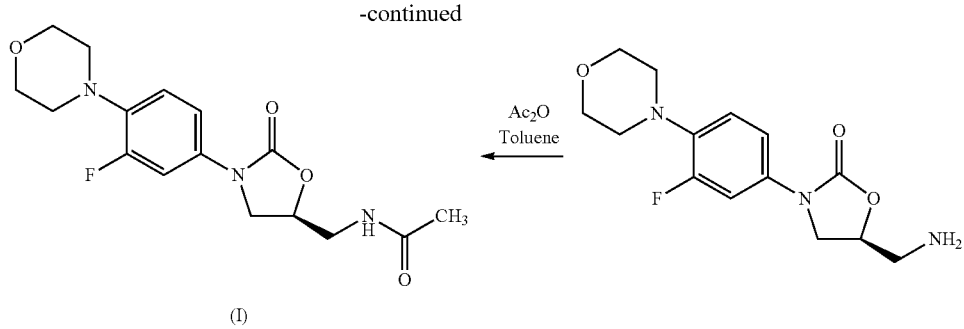

(I)

WO2007116284 discloses a process for preparing Linezolid, which is depicted in the scheme-V below, by reacting a compound of structure (1) with a compound of structure (2) at a temperature range from ambient temperature to about 65° C. to provide a compound of structure (3), which is hydrolyzed and subsequently acylated to give Linezolid:

describes a process for the preparation of 2-[(2)-oxiran-2-ylmethyl]-1H-isoindole-1,3(2H)-dione comprising the reaction of potassium phthalimide with epibromohydrin in the presence of gaseous or aqueous hydrohalogen acids. This process is schematically shown below:

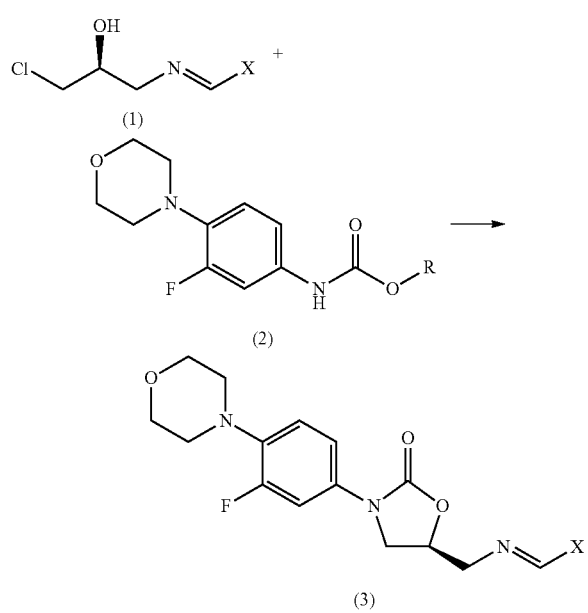

X = chlorophenyl, bromophenyl or 2,4-dichlorophenyl
R = benzyl, C1-8alkyl

The disadvantages of this process is that it involves an additional reaction for the preparation of the compound of structure (1). Schiff's bases are sensitive to water, so that it may not lead to a formation of pure compound (1), which enhances impurity and byproducts formation.

(S)-Glycidyl phthalimide known as 2-[(2S)-Oxiran-2-ylmethyl]-1H-isoindole-1,3(2H)-dione of formula (IX) is a key intermediate used in all synthetic routes of Linezolid.

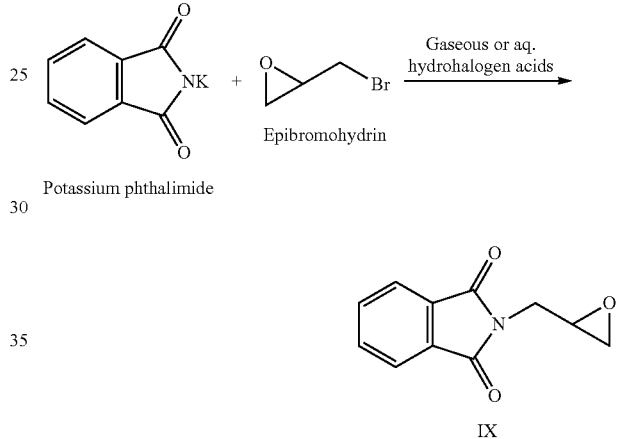

2-[(2)-Oxiran-2-ylmethyl]-1H-isoindole-1,3(2H)-dione (I) was first mentioned in *Compt. rend.* 1930, 190, 495-6, which U.S. Pat. No. 5,608,110 discloses a process for the preparation of 2-[(2S)-oxiran-2-ylmethyl]-1H-isoindole-1,3(2H)-dione (I) comprising the reaction of phthalimide with (S)-(+)-epichlorohydrin under reflux in ethyl acetate/hexane under a nitrogen atmosphere to get (S)-1-chloro-3-phthalimido-2-propanol which is cyclized in presence of NaH/THF.

The above process is schematically shown below:

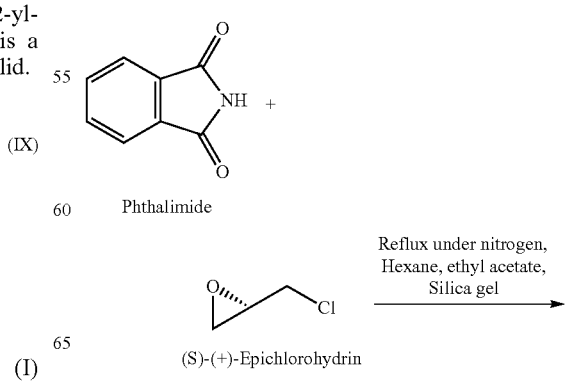

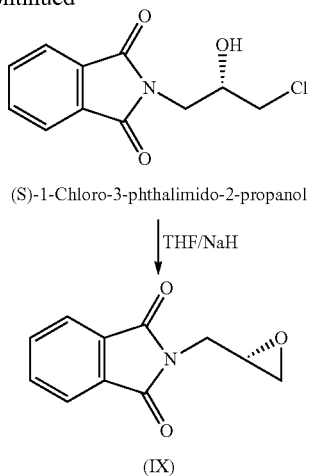

(S)-1-Chloro-3-phthalimido-2-propanol

↓ THF/NaH (IX)

U.S. Pat. No. 6,875,875 discloses a process for the preparation of 2-[(2S)-oxiran-2-ylmethyl]-1H-isoindole-1,3 (2H)-dione (I) comprising the reaction of phthalimide with (S)-epichlorohydrin in the presence of an alkali metal carbonate, an alkali metal hydrogen carbonate or a quaternary ammonium salt to get (S)-1-chloro-3-phthalimido-2-propanol which is cyclized in the presence of metal alkoxides. This process is schematically shown as below:

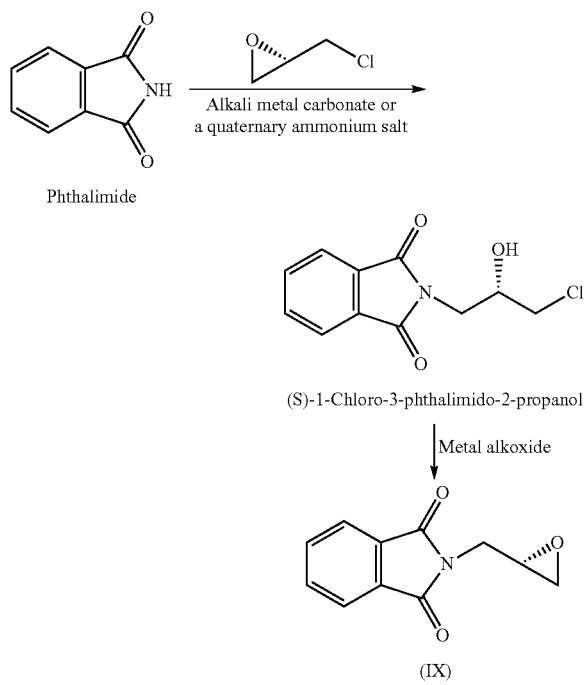

Probably due to the fact that the processes for the synthesis of (S)-glycidyl phthalimide described in U.S. Pat. No. 5,608,110 and U.S. Pat. No. 6,875,875 are carried out under reflux and require high temperatures, the abovementioned approaches yield low optical purities. Ultimately, this issue of the prior art processes results in products (linezolid) with reduced optical purity, and the required purification in order to obtain the desired pure product (such as silica gel column chromatography) is complicated, their industrial application it is difficult and generates a large amount of waste. These problem are in particular addressed by the present invention.

Hence, the use of gaseous or aqueous hydro halogen acids or alkali metal carbonates, alkali metal hydrogen carbonate or a quaternary ammonium salt may not feasible and not economical for industrial production in the preparation of (S)-glycidyl phthalimide.

In their search of an eco-friendly, industrial feasible process for preparing (S)-glycidyl phthalimide our inventors surprisingly came across the benefits of using primary or secondary amines in the condensation reaction. None of the above prior-art processes teaches or suggests the use of primary or secondary organic bases for the preparation of (S)-glycidyl phthalimide There is consequently a need for an alternative method for the preparation of Linezolid and its intermediates, which does not involve the problems described above. Therefore, there is a need in the art for a simple and facile process for the synthesis of Linezolid, and our inventors have developed a cost-effective and industrially viable process.

OBJECTIVE OF THE INVENTION

The main objective of the present invention is to provide a cost-effective and commercially feasible process for the preparation of Linezolid.

Another objective of the present invention is to provide a process for the preparation of the (S)—N-[[3-[3-fluoro-4-[4-morpholinyl]phenyl]-2-oxo-5-oxazolidinyl]methyl] phthalimide and (S)-glycidyl phthalimide intermediates, which employs less expensive, easily available and eco-friendly reagents.

SUMMARY OF THE INVENTION

In one aspect of the present invention an improved process for the preparation of (S)—N-[[3-[3-fluoro-4-[4-morpholinyl]phenyl]-2-oxo-5-oxazolidinyl]methyl]phthalimide of formula (VI) is provided

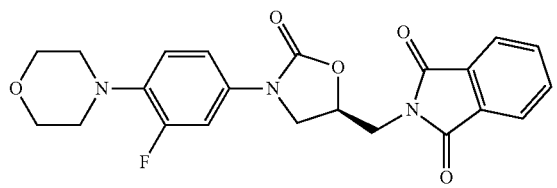

which comprises reacting a carbamate compound of formula (III)

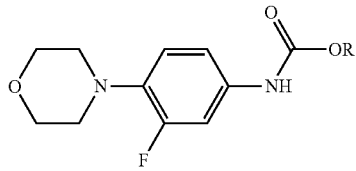

wherein R represents hydrogen, $C_1$-$C_5$ alkyl, aryl, aralkyl; with (S)-glycidyl phthalimide of formula (IX)

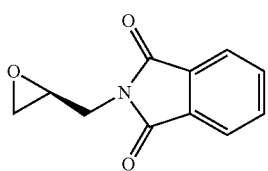

(IX)

in the presence of alkali metal iodides (or) metal hydrides (or)
in the presence of lithium tertiary butoxide in the range 0.2-0.4 mole equivalents based on carbamate compound of formula (III)

In another aspect the present invention provides an improved process for the preparation of the compound of formula (I) comprising the steps of;
a) reacting the compound of formula (III) with (S)-Glycidyl Phthalimide of formula (IX) in the presence of alkali metal iodides (or) metal hydrides to give a compound of formula (VI)
b) subjecting the compound of formula (VI) with aqueous methyl amine or hydrazine hydrate,
c) acylating the product of step b), and
d) isolating the compound of formula (I).

The above synthetic process is illustrated by the following Scheme

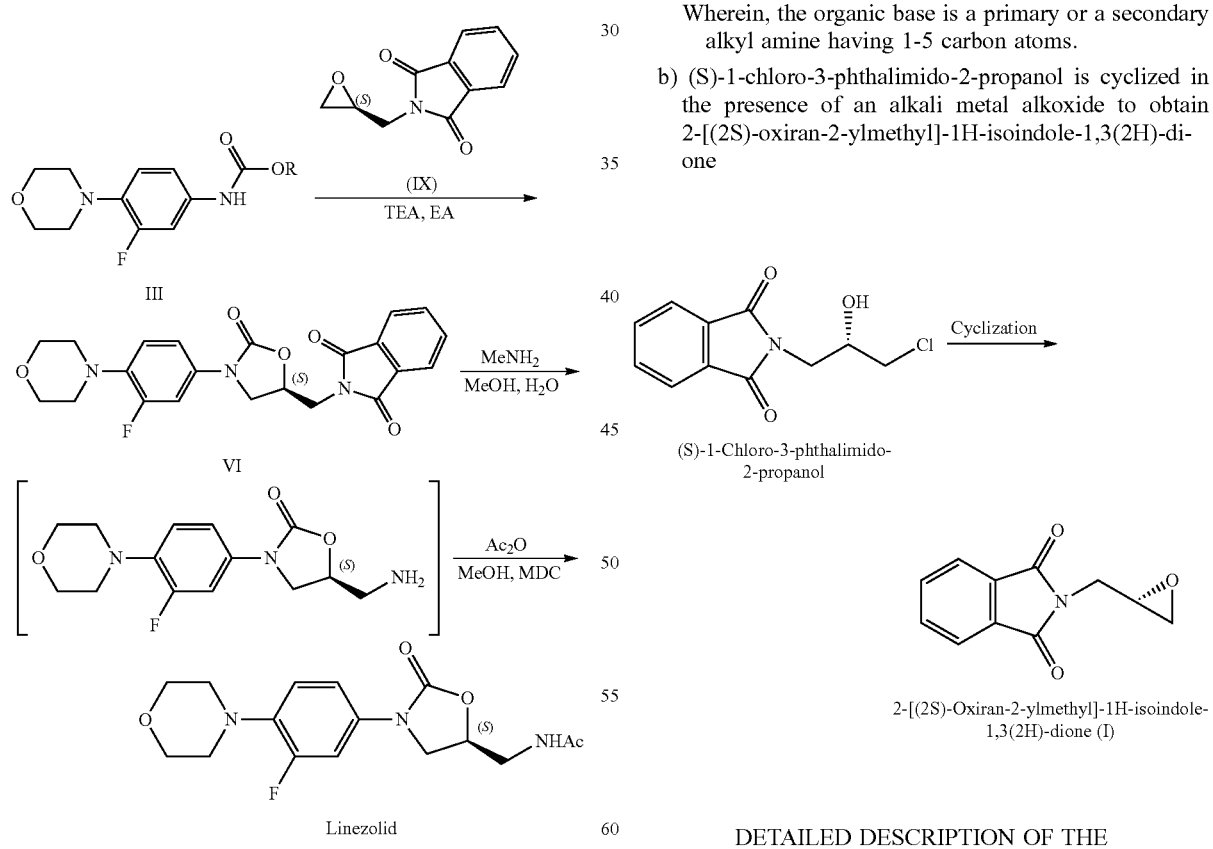

Linezolid

R = alkyl or aryl

In yet another aspect the present invention provides an improved process for the preparation of 2-[(2S)-oxiran-2-ylmethyl]-1H-isoindole-1,3(2H)-dione of formula (IX) comprising the steps of:

a) reacting 1H-isoindole-1,3(2H)-dione or phthalimide with (S)-epichlorohydrin in the presence of an organic base in an organic solvent to obtain (S)-1-chloro-3-phthalimido-2-propanol.

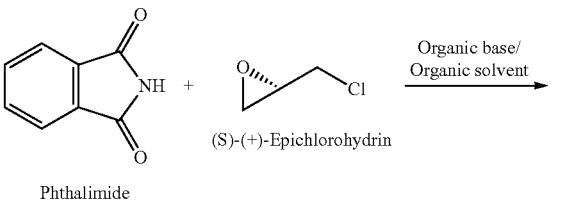

Phthalimide            (S)-(+)-Epichlorohydrin

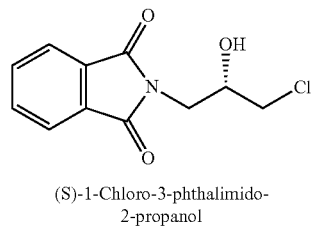

(S)-1-Chloro-3-phthalimido-2-propanol

Wherein, the organic base is a primary or a secondary alkyl amine having 1-5 carbon atoms.

b) (S)-1-chloro-3-phthalimido-2-propanol is cyclized in the presence of an alkali metal alkoxide to obtain 2-[(2S)-oxiran-2-ylmethyl]-1H-isoindole-1,3(2H)-dione 2-[(2S)-Oxiran-2-ylmethyl]-1H-isoindole-1,3(2H)-dione (I)

DETAILED DESCRIPTION OF THE INVENTION

An embodiment of the present invention provides an improved process for the preparation of (S)—N-[[3-[3-fluoro-4-[4-morpholinyl]phenyl]-2-oxo-5-oxazolidinyl]Amethyl] phthalimide of formula (VI)

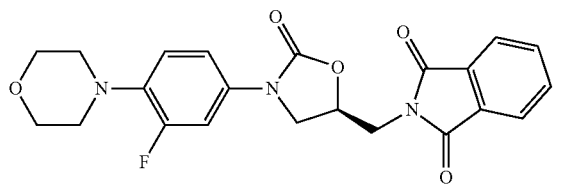

which comprises reacting the carbamate compound of formula (III)

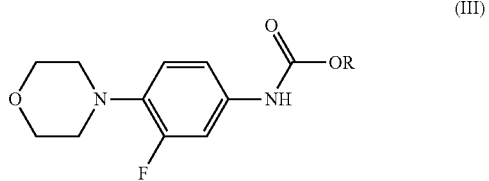

wherein R represents hydrogen, $C_1$-$C_5$ alkyl, aryl, aralkyl; with (S)-glycidyl phthalimide of formula (IX)

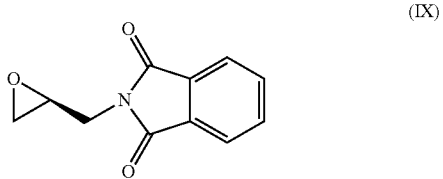 [SMILES: O=C1c2ccccc2C(=O)N1C[C@H]1CO1]

in the presence of alkali metal iodides (or) metal hydrides (or)
in the presence of lithium tertiary butoxide used in the range 0.2-0.4 mole equivalents based on the carbamate compound of formula (III)

In another embodiment, the reaction is carried using an alkali metal iodide and in the presence or absence of a solvent at a temperature in the range of 60 to 120° C. The reaction is carried out for a period of 10 to 14 hours.

In another embodiment, the reaction is carried using a lithium tertiary butoxide used in the range 0.2-0.4 mole equivalents in the presence of a suitable solvent at a temperature in the range of 40 to 100° C. The reaction is carried out for a period of 4 to 12 hours.

According to an embodiment of the present invention, the suitable alkali metal iodides are selected from lithium iodide, sodium iodide, potassium iodide and the like; the suitable solvent is selected from alcohols such as methanol, ethanol, isopropyl alcohol, and the like or mixture thereof; ketones, such as methyl isobutyl ketone, methyl ethyl ketone, n-butanone, and the like; halogenated solvents, such as dichloromethane, ethylene dichloride, chloroform, and the like; esters, such as ethyl acetate, n-propyl acetate, isopropyl acetate, and the like; hydrocarbon solvents, such as toluene, xylene, cyclohexane, and the like; ethers, such as 1,4-dioxane, tetrahydrofuran, and the like; and amides such as N,N-dimethylformamide, N,N-dimethyl acetamide and the like or dimethylsulfoxide or mixture of solvents thereof.

In yet another embodiment of the present invention is the improved process for the preparation of the compound of formula (I) comprises the steps of;

a) reacting the compound of formula (III) with (S)-Glycidyl phthalimide of formula (IX) in the presence of an alkali metal iodide or a metal hydride to give a compound of formula (VI),
b) subjecting the compound of formula (VI) with aqueous methyl amine or hydrazine hydrate,
c) acylating the product of step b), and
d) isolating the compound of formula (I).

According to an embodiment of the present invention, the reaction between the compound of formula (III) with (S)-Glycidyl phthalimide of formula (IX) is carried out in the presence of a suitable alkali metal iodide (or) a metal hydride and a solvent at a suitable temperature to give a compound of formula (VI); this compound is subjected to deprotection with hydrazine hydrae (or) aqueous methyl amine to give (S)-5-aminomethyl-3-(3-fluoro-4-morpholin-4-yl-phenyl)-oxazolidin-2-one, which is subsequently acylated with acetic anhydride or acetyl chloride to give (S)—N-[[3-(3-fluoro-4-morpholinylphenyl)-2-oxo-5-oxazolidinyl]methyl] acetamide (Linezolid) of formula I.

According to an embodiment of the present invention, the reaction between the compound of formula (III) with (S)-glycidyl phthalimide of formula (IX) is carried out in the presence of a suitable metal hydride and a solvent at a suitable temperature to give a compound of formula (VI); the reaction is completed within a shorter time span and provides good quantity of yield and high purity According to an embodiment, the alkali metal iodide is selected from lithium iodide, sodium iodide, potassium iodide and the like; the metal hydride is selected from sodium hydride, lithium hydride or magnesium hydride.

According to an embodiment of the present invention, the suitable solvent is selected from alcohols such as methanol, ethanol, isopropyl alcohol, and the like or mixture thereof; ketones, such as methyl isobutyl ketone, methyl ethyl ketone, n-butanone, and the like; halogenated solvents, such as dichloromethane, ethylene dichloride, chloroform, and the like; esters, such as ethyl acetate, n-propyl acetate, isopropyl acetate, and the like; hydrocarbon solvents, such as toluene, xylene, cyclohexane, and the like; ethers, such as 1,4-dioxane, tetrahydrofuran, and the like; and amides such as N,N-dimethylformamide, N,N-dimethyl acetamide and the like or dimethyl sulfoxide or mixture of solvents thereof In an embodiment, the present invention further involves a conversion of the compound of formula (VI) to Linezolid of formula (I), which involves the conversion of the phthalimide compound of formula (VI) to an amine, followed by acylation to yield Linezolid using conventional methods known in the prior art.

According to one embodiment of the present invention, the acylation is carried out in the presence of acetic anhydride or acetyl chloride.

The reaction is performed at or below boiling temperature of the solvent, preferably between 10° C. and boiling temperature of the solvent and even more preferably at the boiling temperature of the solvent. The time required for completion of the reaction depends on factors such as the solvent used and the applied temperature.

According to an embodiment, the present invention relates to an improved process for the preparation of 2-[(2S)-oxiran-2-ylmethyl]-1H-isoindole-1,3(2H)-dione of formula IX comprising the steps of:

a) reacting phthalimide with (S)-(+)-Epichlorohydrin in the presence of an organic base in an organic solvent at a temperature of 60° C. to obtain (S)-1-chloro-3-phthalimido-2-propanol.

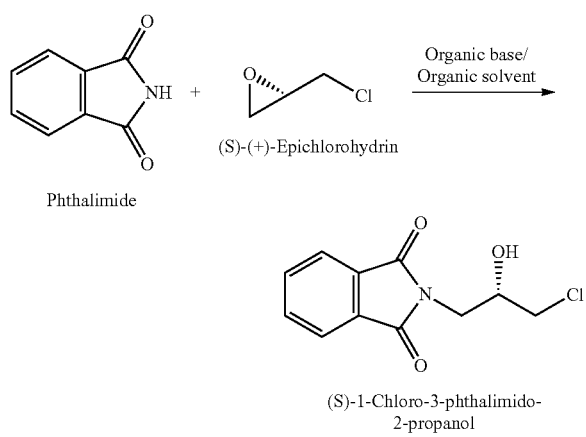

wherein, the organic base is a primary or a secondary alkyl amine having 1-5 carbon atoms.

The organic base is selected from a primary or a secondary alkyl amine having 1-5 Carbon atoms such as methylamine, ethylamine, ethyl methylamine, diethylamine, dipropylamine, dibutylamine, preferably diethylamine.

The organic solvent is selected from the group comprising alcohols, ethers, esters, nitriles having $C_1$-$C_4$ carbon atoms; preferably alcohols.

The alcohol is selected from methanol, ethanol, propanol, isopropanol, butanol; the ether solvents are selected from diethyl ether, tetrahydrofuran etc.; the ester solvents are selected from ethyl acetate, methyl acetate, etc.; nitriles are selected from acetonitrile, propionitrile, butyronitrile etc.

b) (S)-1-chloro-3-phthalimido-2-propanol is cyclized in the presence of an alkali metal alkoxide to obtain 2-[(2S)-oxiran-2-ylmethyl]-1H-isoindole-1,3(2H)-dione

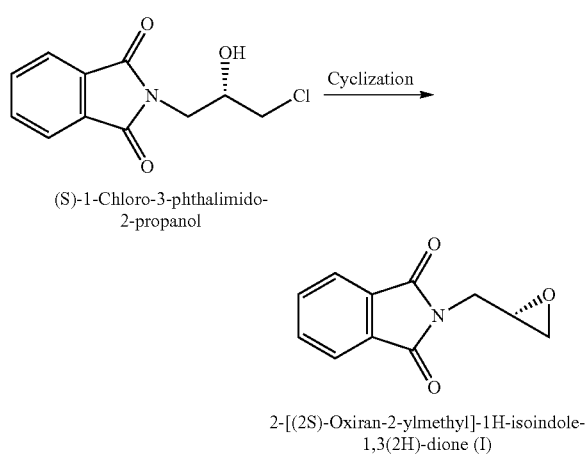

Cyclization of (S)-1-chloro-3-phthalimide-2-propanol will produce 2-[(2S)-oxiran-2-ylmethyl]-1H-isoindole-1,3-(2H)-dione.

Cyclization is carried out in the presence of an alkali metal alkoxide as described in U.S. Pat. No. 6,875,875.

Linezolid produced according to the present invention may be in amorphous form or in crystalline forms I or II.

According to the present invention, the compound of formula (I) or Linezolid has a HPLC purity of not less than 99%.

Advantages of the Present Invention

1. The present invention is a simple, operation friendly and industrially applicable process.
2. The process is commercially viable and provides the compounds in high yield, which makes the process cost effective
3. The reaction sequence of the present invention is carried out in a shorter time span
4. The present invention provides the compounds of formulas (I), (VI) and (IX) with high purity and less impurities.

The process details of the invention are provided in the examples given below, which are provided by way of illustration only and therefore should not be construed to limit the scope of the invention.

Experimental Procedure

Example 1

Preparation of 2-[(2S)-oxiran-2-ylmethyl]-1H-isoindole-1,3(2H)-dione

To a suspension of 1H-isoindole-1,3(2H)-dione (100 g, 0.68 moles) and methylamine (10 g) in isopropanol (200 ml), S-epichlorohydrin (100 g 1.08 moles) was added and the mixture was heated to 60° C. and maintained for 5 h at the same temperature. 30% Sodium methoxide in methanol (160 g) was added portion wise at 10-15° C. to the reaction mass, the temperature was raised to 25-30° C. and the reaction mass was stirred for 2-3 h at the same temperature. After completion of the reaction, water (600 ml) was added, the reaction mixture was stirred for 10 min, the solid was filtered off and washed with water to obtain the title compound.

Weight: 107 g (77.5%)

Example 2

Preparation of 2-[(2S)-oxiran-2-ylmethyl]-1H-isoindole-1,3(2H)-dione

To a suspension of 1H-isoindole-1,3(2H)-dione (100 g, 0.68 moles) and diethyl amine (10 g) in ethanol (200 ml), S-epichlorohydrin (100 g 1.08 moles) was added and the mixture was heated to 60° C. and maintained for 5 h at the same temperature. 30% sodium methoxide in methanol (160 g) was added portion wise at 10-15° C. to the reaction mass, the temperature was raised to 25-30° C. and the reaction mass was stirred for 2-3 h at the same temperature. After completion of the reaction, water (600 ml) was added, the reaction mixture was stirred for 10 min, the solid was filtered off and washed with water to obtain the title compound.
Weight: 107 g (77.5%)

Example-3

Preparation of (S)-2-[3-(3-fluoro-4-morpholin-4-yl-phenyl)-2-oxo-oxazolidin-5-ylmethyl]-isoindole-1,3-dione A mixture of methyl (3-fluoro-4-morpholinophenyl) carbamate (50 g, 0.196 moles) in ethyl acetate (100 ml) was stirred for 10 min at a temperature of 25 to 30° C. 2-[(2S)-oxiran-2-ylmethyl]-1H-isoindole-1,3(2H)-dione (50 g, 0.246 moles) and lithium tertiary butoxide (5.0 g, 0.0624 moles) were added in one lot at a temperature of 25 to 30° C., and the temperature was slowly raised to 70-75° C. and maintained for about 6-8 hrs. The reaction mixture was cooled to ambient temperature, ethyl acetate (50 ml) was added, and the resultant slurry was stirred for 30 min at a temperature of 25-30° C. The solid was filtered off. The resultant crude solid was added to ethyl acetate (250 ml) at a temperature of 25-30° C. and heated to 70-75° C. The slurry was stirred for 15-20 min, cooled to 25-30° C. and stirred for 30 min. The obtained solid was filtered and washed with ethyl acetate (50 ml) to get pure (5S)2-[3-(3-fluoro-4-morpholin-4-yl-phenyl)-2-oxo-oxazolidin-isoindole-1,3-dione. Yield: 70 g (85% yields on theoretical)

Example-4

Preparation of (S)-2-[3-(3-fluoro-4-morpholin-4-yl-phenyl)-2-oxo-oxazolidin-5-ylmethyl]-isoindole-1,3-dione A mixture of methyl (3-fluoro-4-morpholinophenyl) carbamate (50 g, 0.196 moles) in dimethyl formamide (75 ml), 2-[(2S)-oxiran-2-ylmethyl]-1H-isoindole-1,3(2H)-dione (50 g, 0.246 moles) and lithium tertiary butoxide (5.0 gm, 0.0624 moles) was heated to 70-75° C. and maintained at the same temperature for about 4-6 hrs. The reaction mixture was allowed to cool to 26° C., methanol (250 ml) was added and the slurry was stirred for 30 min at 25-30° C. The resultant solid was filtered and washed with methanol (50 ml). The obtained crude solid was recrystallized with ethyl acetate to get pure (5S)-2-[3-(3-Fluoro-4-morpholin-4-yl-phenyl)-2-oxo-oxazolidin-isoindole-1,3-dione. Yield: 65 g (77.7%)

Example-5

Preparation of (S)-2-[3-(3-fluoro-4-morpholin-4-yl-phenyl)-2-oxo-oxazolidin-5-ylmethyl]-isoindole-1,3-dione To a mixture of methyl (3-fluoro-4-morpholinophenyl) carbamate (100 g, 0.392 moles), in dimethyl formamide (200 ml) 2-[(2S)-oxiran-2-ylmethyl]-1H-isoindole-1,3(2H)-dione (100 g, 0.492 moles) and lithium tertiary butoxide (5.0 gm, 0.0625 moles) were added in one lot at a temperature of 25 to 30° C. The temperature was raised to 80-85° C. and maintained for about 4-6 hrs. The reaction mixture was cooled to ambient temperature, followed by addition of purified water (500 ml) and stirred for 30 min at 25-30° C. The resultant solid was filtered off and washed with purified water (100 ml). The obtained crude solid was recrystallized from ethyl acetate to get pure (5S)-2-[3-(3-fluoro-4-morpholin-4-yl-phenyl)-2-oxo-oxazolidin-isoindole-1,3-dione.
Yield: 140 g (85%)

Example-6

Preparation of (S)-2-[3-(3-fluoro-4-morpholin-4-yl-phenyl)-2-oxo-oxazolidin-5-ylmethyl]-isoindole-1,3-dione To a mixture of methyl-(3-fluoro-4-morpholinophenyl) carbamate (20 g, 0.0784 moles), 2-[(2S)-oxiran-2-ylmethyl]-1H-isoindole-1,3(2H)-dione (20 g, 0.0984 moles) in dimethyl formamide (80 ml) sodium iodide (4.0 g) was added in one lot at a temperature of 25 to 30° C., and the temperature was slowly raised to 110-115° C. The reaction mixture was maintained at 110-115° C. for about 6 to 8 hrs and cooled to ambient temperature. Water (200 ml) was added, the mixture was stirred for 30 min at a temperature of 25-30° C. and the solid was filtered off. The obtained crude solid was recrystallized from methanol (20 ml) to get pure (5S)2-[3-(3-Fluoro-4-morpholin-4-yl-phenyl)-2-oxo-oxazolidin-isoindole-1,3-dione. Yield: 25 g (75%)

Example-7

Preparation of (S) 2-[3-(3-fluoro-4-morpholin-4-yl-phenyl)-2-oxo-oxazolidin-5-ylmethyl]-isoindole-1,3-dione To a mixture of methyl (3-fluoro-4-morpholinophenyl) carbamate (25 g, 0.098 moles) in tetrahydrofuran (50 ml) 2-[(2S)-oxiran-2-ylmethyl]-1H-isoindole-1,3(2H)-dione (25 g, 0.123 moles) was added and the mixture was stirred for 10 min at a temperature of 25 to 30° C.; followed by lot wise addition of sodium hydride (1.2 gm, 0.05 moles) at 25 to 30° C. The temperature was slowly raised to 50-60° C. and maintained at the same temperature for about 2-3 hrs. The reaction mass was cooled to below 20° C., quenched with 25 ml methanol to decompose the excess sodium hydride. The solvent was distilled off and methanol was added (125 ml). The resulting slurry was stirred for 30 min at 25 30° C. and filtered. The obtained solid was taken into ethyl acetate (125 ml) and the slurry was heated to 70-75° C., stirred for 15-20 min, cooled to 25-30° C. and filtered. The resulting solid was washed with ethyl acetate (25 ml) to get the pure (5S)-2-[3-(3-fluoro-4-morpholin-4-yl-phenyl)-2-oxo-oxazolidin-isoindole-1,3-dione. Yield: 34 g (77%)

Example-8

Preparation of (S)-2-[3-(3-Fluoro-4-morpholin-4-yl-phenyl)-2-oxo-oxazolidin-5-ylmethyl]-isoindole-1,3-dione To a mixture of methyl (3-fluoro-4-morpholinophenyl) carbamate (25 g, 0.098 moles) in N,N-dimethyl formamide (50 ml) 2-[(2S)-oxiran-2-ylmethyl]-1H-isoindole-1,3(2H)-dione (25 g, 0.123 moles) was added and stirred for 10 min at a temperature of 25 to 30° C.; followed by a lot wise addition of sodium hydride (1.2 gm, 0.05 moles) at 25 to 30° C. The temperature was slowly raised to 50-60° C. and maintained for about 2-3 hrs. The reaction mass was cooled to below 20° C., quenched with 25 ml methanol to decompose the excess sodium hydride. Further methanol (125 ml) was added and the resulting slurry was stirred for 30 min at 25-30° C. and filtered. The obtained solid was taken into ethyl acetate (125 ml) and heated to 70-75° C. The slurry was stirred for 15-20 min, cooled to 25-30° C. and filtered. The resultant solid was washed with ethyl acetate (25 ml) to get pure (5S)-2-[3-(3-fluoro-4-morpholin-4-yl-phenyl)-2-oxo-oxazolidin-isoindole-1,3-dione. Yield: 32 g (75%)

Example-9

Preparation of N-({(5S)-3-[3-fluoro-4-(morpholin-4-yl) phenyl]-2-oxo-1,3-oxazolidin-5-yl} methyl) acetamide (Linezolid)

To a mixture of methanol (100 ml), DM water (400 ml) and (S) 2-[3-(3-fluoro-4-morpholin-4-yl-phenyl)-2-oxo-oxazolidin-5-ylmethyl]-isoindole-1,3-dione (100 g, 0.212 moles) a methyl amine solution (47 g) was added at a temperature of 25-30° C. The reaction mixture was stirred and the temperature was slowly raised to 80-85° C. and maintained for 2-3 hours. The reaction mixture was cooled to 25-30° C. and dichloromethane (500 ml) was added. The reaction mixture was stirred for 15 min and the layers were separated. MDC was distilled out completely under atmospheric pressure to get the residual product (5S)-5-(amino methyl)-3-[3-fluoro-4-(morpholin-4-yl) phenyl]-1,3-oxazolidin-2-one. Dichloromethane (400 ml) was added to the residue and acetic anhydride (25 g) was slowly added at a temperature of 25-30° C. over a period of 60 min. After completion, 5% aqueous sodium bicarbonate solution was slowly added to the reaction mixture. After stirring for 15 min the two layers were separated. The dichloromethane layer was washed with DM Water (200 ml). The dichloromethane layer was filtered through hyflo and the solvent was distilled off completely under vacuum below 40° C. Cyclohexane (500 ml) was added to the residue and heated to 45-50° C. The obtained slurry was cooled to 20-25° C. and stirred for 60 min. filtered the solid, washed with cyclohexane (200 ml) and dried the solid at 45-55° C. to furnish pure crystalline N-({(5S)-3-[3-fluoro-4-(morpholin-4-yl)phenyl]-2-oxo-1,3-oxazolidin-5-yl}methyl)acetamide (Linezolid) (53 g 75%).

Example-10

Preparation of N-({(5S)-3-[3-fluoro-4-(morpholin-4-yl) phenyl]-2-oxo-1,3-oxazolidin-5-yl} methyl) acetamide (Linezolid)

To a mixture of methanol (100 ml), DM water (400 ml) and (S) 2-[3-(3-fluoro-4-morpholin-4-yl-phenyl)-2-oxo-oxazolidin-5-ylmethyl]-isoindole-1,3-dione (100 g, 0.212 moles) hydrazine hydrate (50 g) was added at a temperature of 25-30° C. The mixture was stirred and the temperature was slowly raised to 70-75° C. and maintained for 2-3 hours. The reaction mixture was cooled to 25-30° C. and dichloromethane (250 ml) was added. The reaction mixture was stirred for 15 min and the two layers were separated. MDC was distilled off completely under atmospheric pressure to get the residual product (5S)-5-(aminomethyl)-3-[3-fluoro-4-(morpholin-4-yl) phenyl]-1,3-oxazolidin-2-one. Dichloromethane (200 ml) was added to the residue and acetic anhydride (13 g) was slowly added at 25-30° C. over a period of 60 min. The reaction mixture was stirred for 60 min at 25-30° C. After completion of the reaction, 5% aqueous sodium bicarbonate solution was slowly added to the reaction mixture, which was stirred for 15 min. The two layers were separated. The dichloromethane layer was washed with water (100 ml). The dichloromethane layer was filtered through hyflo and the solvent was distilled off completely under vacuum below 40° C. Cyclohexane (250 ml) was added to the residue and the mixture was heated to 45-50° C. The slurry obtained was cooled to 20-25° C. and stirred for 60 min. The solid was filtered and the solid washed with cyclohexane (100 ml) and dried at 45-55° C. to furnish pure crystalline 55 g of N-({(5S)-3-[3-fluoro-4-(morpholin-4-yl)phenyl]-2-oxo-1,3-oxazolidin-5-yl}methyl)acetamide (Linezolid).

Example 11

Preparation of N-({(5S)-3-[3-fluoro-4-(morpholin-4-yl) phenyl]-2-oxo-1,3-oxazolidin-5-yl} methyl) acetamide (Linezolid)

Methyl amine solution (50 g) was added to a mixture of methanol (100 ml), DM water (400 ml) and (5S) 2-[3-(3-Fluoro-4-morpholin-4-yl-phenyl)-2-oxo-oxazolidin-5-ylmethyl]-isoindole-1,3-dione (100 g 0.235 moles) at a temperature of 25-30° C. The reaction mixture was stirred and the temperature was slowly raised to 80-85° C. and maintained for 2-3 hours. The reaction mixture was allowed to cool to 25-30° C., dichloromethane (500 ml) was added and the mixture was stirred for 15 min to separate the layers. Purified water (500 ml) was added to the MDC layer and the mixture was acidified to pH 2.0-3.0 with dilute hydrochloric acid and stirred for 10-15 min. The two layers were separated and basified with aqueous ammonia to pH 10.0-11.0 to separate the MDC layer. The solvent of the isolated organic layer was distilled off completely under atmospheric pressure to get the residual product of (5S)-5-(amino methyl)-3-[3-fluoro-4-(morpholin-4-yl) phenyl]-1,3-oxazolidin-2-one. Dichloroinethane (400 ml) was added to the residue and acetic anhydride (25 g) was slowly added at 25-30° C. over a period of 60 min. The reaction mixture was stirred for 60 min at 25-30° C. After completion of reaction, 5% aqueous sodium bicarbonate solution was slowly added to the reaction mixture, which was stirred for 15 min. The two layers were separated and the dichloromethane layer was washed with DM Water (200 ml). The dichloromethane layer was filtered through hiflo and dichloromethane was distilled off completely under vacuum below 40° C. Cyclohexane (500 ml) was added to the residue and the mixture was heated to 45-50° C. The slurry obtained was cooled to 20-25° C. and stirred for 60 min. The solid obtained was filtered, washed with cyclohexane (200 ml) and dried at 45-55° C. to furnish pure crystalline N-({(5S)-3-[3-fluoro-4-(morpholin-4-yl) phenyl]-2-oxo-1,3-oxazolidin-5-yl} methyl)acetamide (Linezolid) (53 g, 75%).

We claim:
1. A process for the preparation of the compound of formula (I)

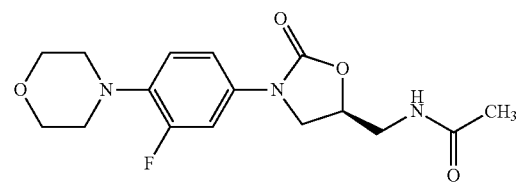

comprising the steps of
a) reacting a compound of formula (III) with (S)-Glycidylphthalimide of formula (IX) in the presence of an alkali metal iodide or a metal hydride to give the compound of formula (VI)

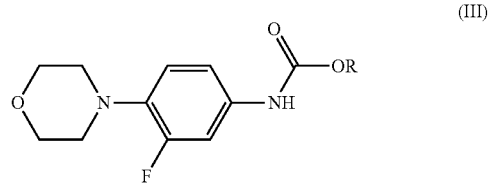

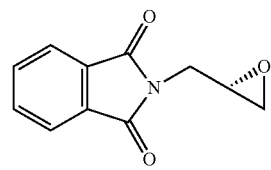

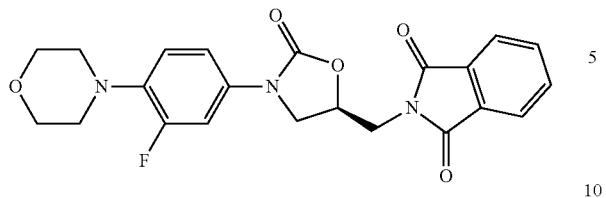

wherein R represents hydrogen, $C_1$-$C_5$ alkyl, aryl, or aralkyl b) treating the compound of formula (VI) with aqueous methyl amine or hydrazine hydrate, c) acylating the product of step b) with an acylating agent, and d) isolating the compound of formula (I).

2. The process according to claim 1, wherein the alkali metal iodide is selected from the group consisting of lithium iodide, sodium iodide and potassium iodide; wherein the metal hydride is selected from the group consisting of lithium hydride, sodium hydride and magnesium hydride; and wherein the acylating agent is selected from the group consisting of acetic anhydride and acetyl chloride.

3. The process according to claim 1, wherein step a) is carried out in the presence of a solvent selected from the group consisting of alcohols, ketones, halogenated solvents, esters, hydrocarbon solvents, ethers, amides, and dimethyl sulfoxide.

* * * * *